United States Patent
Lee et al.

(10) Patent No.: US 6,545,159 B2
(45) Date of Patent: Apr. 8, 2003

(54) VINYL-PHENYL PYRIDINE MONOMERS AND POLYMERS PREPARED THEREFROM

(75) Inventors: Jae-Suk Lee, Kwangju (KR); Jun-Hwan Ahn, Kwangju (KR); Young-Sun Cho, Kwangju (KR); Nam-Goo Kang, Kwangju (KR); Hye-Kyong Lee, Kwangju (KR)

(73) Assignee: Kwangju Institute of Science and Technology, Kwangju (KR)

( * ) Notice: Subject to any disclaimer, the term of this patent is extended or adjusted under 35 U.S.C. 154(b) by 0 days.

(21) Appl. No.: 09/925,685

(22) Filed: Aug. 10, 2001

(65) Prior Publication Data

US 2002/0198346 A1 Dec. 26, 2002

(30) Foreign Application Priority Data

Mar. 29, 2001 (KR) ......................................... 2001-16487

(51) Int. Cl.[7] ..................... C07D 213/24; C07D 213/04
(52) U.S. Cl. ........................................ 546/348; 546/350
(58) Field of Search ................................. 546/348, 350

(56) References Cited

PUBLICATIONS

English Abstract, Polymeric Copper Complexes in oxidative coupling reactions, Challa G. et al 1978, vol. 183, pp. 185–193.*

T. Ishizone et al., Anionic Polymerization of Monomers Containing Functional Groups. 7. Anionic Polymerizations of N–Alkyl–N–(4–vinylbenzylidene) amines, Macromolecules, vol. 26, No. 25, pp. 6976–6984. (1993).

Y. Ishino et al., Protection and Polymerization of Functional Monomers. 7. Anionic Living Polymerization of 2–(4–vinylphenyl)–4,4–dimethyl–2–oxazoline; Macromolecules, vol. 19, pp. 2307–2309 (1986).

A. Hirao et al., Protection and Polymerization of Functional Monomers. 18. Synthesis of Well–Defined Poly(vinylphenol), Poly[vinylphenyl) methanol], and Poly [2–(vinlyphenyl) ethanol] by Means of Anionic Living Polymerization of Styrene Derivatives Containing tert–Butyldimethylsily Ethers, Macromolecules, vol. 26, pp. 4995–5003, (1993).

A. Hirao et al., Protection and Polymerization of Functional Monomers. 11. Syntheses of Well–Defined Poly (4–vinylbenzoic acid) by Means of Anionic Living Polymerization of 2–(4–Vinylphenyl)–4, 4–dimethyl–2–oxazoline, Macromolecules, vol. 21, pp. 561–565, (1988).

M.A. Baldo et al., Very high–efficiency green organic light–emitting devices based on electrophosphorescence.

(List continued on next page.)

Primary Examiner—Alan L. Rotman
Assistant Examiner—Rita Desai
(74) Attorney, Agent, or Firm—Finnegan, Henderson, Farabow, Garrett & Dunner, L.L.P.

(57) ABSTRACT

The present invention relates to vinyl-phenyl monomers and polymers prepared therefrom. More particularly, the present invention is to provide the vinyl-phenyl monomers expressed by formula (1) which are capable of various polymerization such as radical polymerization, cation polymerization, anion polymerization and metallocene catalyzed polymerization due to resonance effect of phenyl group and changing characteristics variously and thus, suitable in the synthesis of general-purpose polymers which can be used in photo-functional materials by forming a complex with a metal component having an optical characteristic:

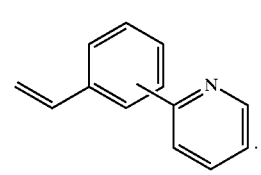

(1)

2 Claims, 8 Drawing Sheets

OTHER PUBLICATIONS

C. Landry, et al., Novel Miscible Blends of Etheric Polyphosphazense with Acidic Polymers, Macromolecules, vol. 26, pp. 35–46 (1993).

T. Ishizone et la., Protection and Polymerization of Functional Monomers. 15. Anionic Living Polymerization of 2–(3–Vinylpheny)–1,3–dioxolane and Related Monomers, Macromolecules, vol. 24, pp. 1449–1454 (1991).

A. Hirao., Protection and Polymerization of Functional Monomers. 103. Syntheses of Well–Defined Poly(4–vinlybenzaldehyde) by the Anionic Living Polymerization of N–[4–Ethenylphenyl) methylene] cyclohexamine, Macromolecules, vol. 20, No. 12, pp 2968–2972 (1977).

J. Lee, et al., Polymerization of Monomers Containing Functional Silyl Groups. 7. Porous Membranes with Controlled Microstructures, Macromolecules, vol. 22, No. 6, pp. 2602–2606 (1989).

S. Nakahama et al., Protection and Polymerization of Functional Monomers: Anionic Living Polymerization of Protected Monomers, Program of Polymer Science, vol. 15, pp. 299–335, (1990).

R. Kwong et al., Organic Light–Emitting Devices Based on Phosphorescent Hosts & Dyes, Advanced Materials, vol. 12, No. 15, pp. 1134–1138(2000.

K. A. King et al., Excited–State Properties of a Triply Ortho–Metalated Iridium (III) Complex., J. American Chemical Society, vol. 107, pp. 1431–1432, (1985).

C. E. Housecroft, Iridium 1993, Coordination Chemistry Reviews 152, pp. 141–156, (1996).

A. J. Lees, Luminescence Properties of Organometallic Complexes, Chem. Rev., vol. 87, pp. 711–743 (1987).

A. Hirao et al., Protection and Polymerization of Functional Monomers: 8.Anionic living polymerization of 4–[2–(trialkyl)silyloxyethyl] styrene as protected 4–(2–hydroxyethyl) styrene, Polymer, 1987, vol. 28, Feb. pp. 303–310.

A. Hirao et al., Polymerization of monomers containing functional groups protected by trialklsilyl groups , $4^{a:}$ Studies on anionic living polymerization of 4–(tert–butyl–dimenthylsilyloxy) styrene; Makromol. Chem. 186, pp. 1157–1166 (1985).

K. Dedeian et al., Sulfur Bridged Incomplete Cubane–Type Mixed–Metal Cluster Compounds of Molybdenum (IV) and Tungsten (IV), Inorganic Chemistry, vol. 30, pp. 1687–1688, (1991).

* cited by examiner

VINYL-PHENYL PYRIDINE MONOMERS AND POLYMERS PREPARED THEREFROM

BACKGROUND OF THE INVENTION

The present invention relates to vinyl-phenyl monomers and polymers prepared therefrom. More particularly, the present invention is to provide the vinyl-phenyl monomers expressed by formula (1) which are capable of various polymerization such as radical polymerization, cationic polymerization, anion polymerization and metallocene catalyzed polymerization due to the resonance effect of phenyl group and changing characteristics variously and thus, suitable in the synthesis of polymers which can be used in photo-functional materials by forming a polymer complex with a metal component having an optical characteristic.

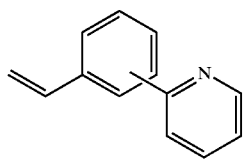

(1)

Continuous polymerization can be divided to ionic polymerization and radical polymerization depending on an initiator. It is difficult to do a controlled polymerization due to side reaction with the radical chain ends in radical polymerization, and reaction termination for the repulsion between the functional groups chain ends in ionic polymerization. Reactivity of radical polymerization varies with resonance stability of vinyl group and that of ionic polymerization varies with the polarity.

(a) Radical Polymerization $CH_2=CH$
|
$X$

Resernance (b) Anionic Polymerization $CH_2=CH$
↓
$X$

Electron-withdrawing group (c) Cationic Polymerization $CH_2=CH$
↑
$X$

Electron-donor group

Monomers used in continuous polymerization can be polymerized by means of radical, cationic or anionic polymerization depending on Q-e value shown in the following table. Especially, either cationic or anionic polymerization can be expected with e value representing the degree of polarity.

| Monomer | Q | e | Cationic Polymerization | Anionic Polymerization |
|---|---|---|---|---|
| $CH_2=CH$<br>\|<br>$OR$ | 0.02 | -1.8 | ⊚ | X |
| 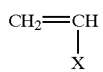 | 0.98 | -1.27 | ⊚ | ○ |
| 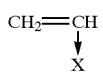 | 1.00 | -0.80 | ○ | ○ |
| $CH_2=CH$<br>\|<br>$C=O$<br>\|<br>$OCH_3$ | 0.42 | 0.62 | X | ○ |
| $CH_2=CH$<br>\|<br>$C\equiv N$ | 0.60 | 1.20 | X | ⊚ |

The polarity of a monomer is important in anionic polymerization because reactivity is highly dependent on the polarity of the monomer. That is, a selection of monomers plays an essential role in the synthesis of block copolymers. A monomer having an electron-withdrawing character in vinyl group is preferable for anionic polymerization. Representative anionic monomers are styrene, α-methylstyrene, butadiene and isoprene which undergo the polymerization with a carbanion having strong reactivity because they have –e values. The order of polymerization is α-methylstyrene, isoprene and styrene.

Polymers having functional groups can be widely used for photo-functional materials. In order to polymerize styrene, butadiene and methacrylate having a variety of functional groups through anionic polymerization, it is required to protect the functional groups during the polymerization to prevent from the termination reaction between carbanion and the functional groups. S. Nakahama et. al have reported that styrene monomer having amine, hydroxy, carbonyl, carboxyl, or mercapto group can be protected with an appropriate protecting group such as trimethyl silyl, t-butyldimethyl silyl, oxazoline and ester groups during the polymerization and the protected functionality is then deprotected to regenerate the original functional group after the polymerization [S. Nakahama, *Prog. Polym. Sci.*, 15, 299 (1990); *Makromol, Chem.*, 186, 1157 (1985); *Polymer*, 28, 303(1987); *Macromolecules*, 19, 2307 (1986); ibid. 26, 4995 (1993); ibid. 26, 35 (1993); *Macromolecules*, 20, 2968 (1987); ibid. 24, 1449 (1991); ibid. 26, 6976 (1993); *Macromolecules*, 19, 2307 (1986); ibid. 21, 561 (1988); ibid. 22, 2602 (1989)]. And further, the research and development of photo conductive and organic light emitting devices using phenylpyridines have been actively studied and some examples have been reported [Alistair J. Lee, *Chem. Rev.* 1987, 87, 711~743; M. A. Baldo, S. Lamansky, P. E. Burrows, M. E. Thompson, S. R. Forrest, *Appl. Phys. Lett.*, 75, 4, (1999); Raymond C. Kwong, Sergey Lamansky, and Mark E. Thompson, *Adv. Mater.,* 2000, 12, No. 15, 1134; Catherine E. Housecroft, *Coordination Chemistry Reviews,* 152, (1996), 141~156; K. Dedeian, P. I. Djurovich, F. O. Garces, G. Carlson, R. J. Watts, *Inorg. Chem.,* 1991, 30, 1687~1688; King, K. A, Spellane, P. J., Watts, R. J., *J. Am. Chem. Soc.,* 1985, 107, 1431].

However, the study of phenylpyridines is limited to only organic molecule and there is no report in the synthesis of the corresponding polymers using phenylpyridine monomers.

The present invention is to provide 2-(4-vinyl-phenyl) pyridine monomers and polymers with controllable molecular weight and molecular structure which can be widely useful for photo-functional materials since said polymers of such monomers is reliable to form a complex of a metal component (iridium, ruthenium and the like).

SUMMARY OF THE INVENTION

Vinyl-phenyl monomers of formula (1) of the present invention are capable of various polymerization such as radical polymerization, cation polymerization, anion polymerization and metallocene catalyzed polymerization due to the resonance effect of the phenyl group.

(1)

The molecular weight and molecular structure of polymers can be controlled during the polymerization and the prepared polymers can further form a complex with various metal components such as iridium, ruthenium and the like to be useful for photo-functional materials.

Therefore, an object of the present invention is to provide vinyl-phenyl pyridine monomers and the preparation method thereof which can be easily introduced to synthesize polymers with the controlled functional groups and thus, such polymers can be applied in the preparation of thin film or fiber depending on the purpose.

Another object of the present invention is to provide the polymers prepared by using the monomers of formula (1).

Further objection of the present invention is to provide a complex of the polymers and iridium, ruthenium or platinum having optical character.

BRIEF DESCRIPTION OF THE INVENTION

DETAILED DESCRIPTION OF THE INVENTION

Figure 1:
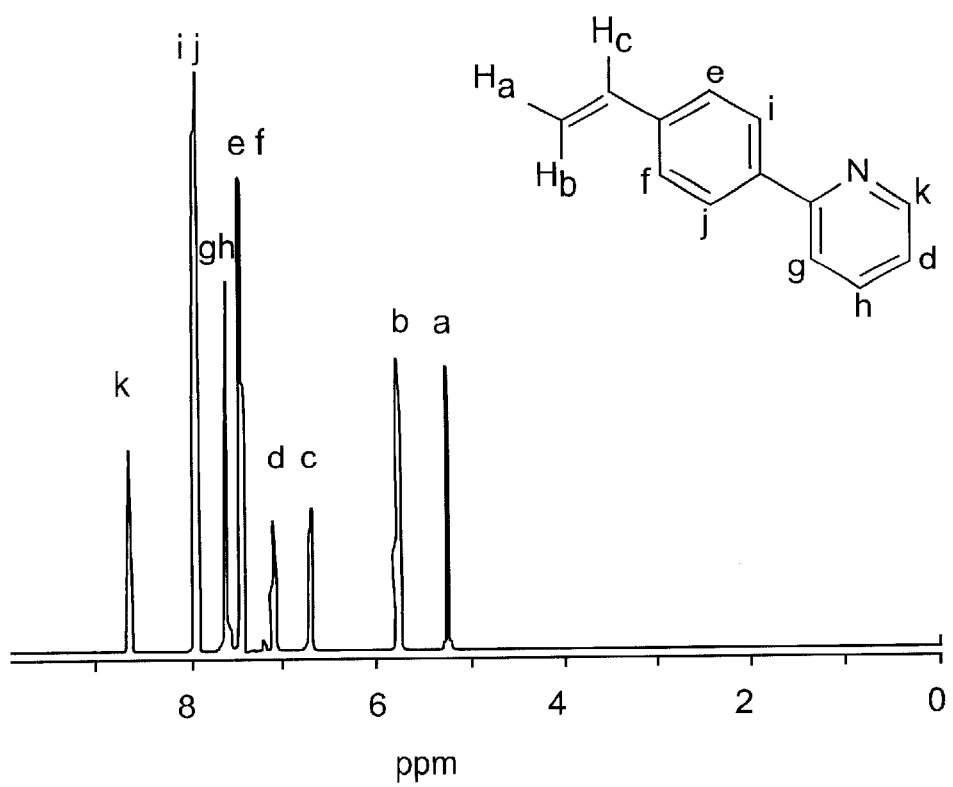
FIG. 1 represents $^1$H-NMR spectrum of 2-(4-vinyl-phenyl)pyridine.

The present invention is characterized by vinyl-phenyl pyridine monomers expressed by the following formula (1).

(1)

The present invention is described in detail as set forth hereunder.

Examples of vinyl-phenyl pyridine monomers of the present invention are 2-(2-vinyl-phenyl)pyridine, 2-(3-vinyl-phenyl)pyridine, and 2-(4-vinyl-phenyl)pyridine.

The vinyl-phenyl pyridine monomers of formula (1) are prepared by the following methods.

The first is Suzuki coupling reaction as shown in Scheme 1.

Scheme 1

In Scheme 1, the vinyl-phenyl pyridine of formula (1) is prepared by Suzuki coupling reaction of vinyl-phenylboronic acid of formula (2) and 2-bromopyridine of formula (3) in the presence of alkali metallic base and palladium catalyst. Examples of alkali metallic base used are sodium carbonate, potassium carbonate, sodium hydroxide and potassium hydroxide. Examples of palladium catalyst are tetrakis(triphenylphosphine)palladium (Pd(PPh$_3$)$_4$) and palladium acetate. Examples of reaction solvent are tetrahydrofuran (THF), N,N-dimethylformamide (DMF), dimethyl sulfoxide (DMSO), and toluene. The Suzuki coupling reaction is performed it a temperature of from 80 to 120° C.

The second is Suzuki coupling reaction and Wittig reaction as shown in Scheme 2.

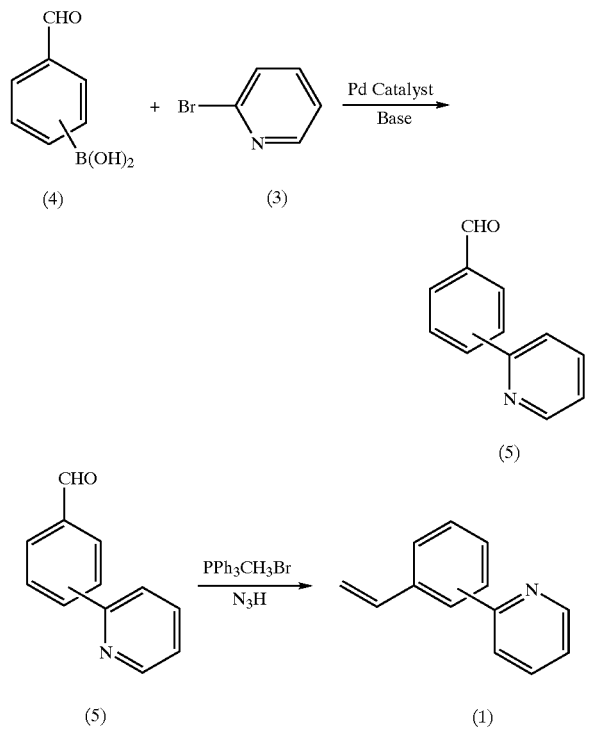

In Scheme 2, formylphenyl pyridine of formula (5) is prepared by Suzuki coupling reaction of formylphenylboronic acid of formula (4) and 2-bromopyridine of formula (3) in the presence of alkali metallic base and palladium catalyst and further, Wittig reaction of the prepared formylphenyl pyridine of formula (5) is performed in the presence of methyltriphenylphosphonium bromide (PPh$_3$CH$_3$Br) and sodium hydride to to yield vinyl-phenyl pyridine of formula (1).

Examples of alkali metallic base used in Suzuki coupling reaction are sodium carbonate, potassium carbonate, sodium hydroxide and potassium hydroxide and examples of palladium catalyst are tetrakis(triphenylphosphine)palladium (Pd(PPh$_3$)$_4$) and palladium acetate. Examples of reaction solvent are tetrahydrofuran (THF), N,N-dimethylformamide (DMF), dimethyl sulfoxide (DMSO), and toluene. The Suzuki coupling reaction is performed at a temperature of from 80 to 120° C. and Wittig reaction is from 90 to 130° C.

Besides Suzuki coupling and Wittig reactions, there are other reactions such as Stille coupling reaction using trimethyltin chloride or tributyltin chloride, Grignard reaction using magnesium and nickel catalyst and coupling reaction using zinc, bipyridine, triphenylphosphine and nickel chloride to prepare vinyl-phenyl pyridine monomers.

The present invention is also characterized by polymers prepared with the vinyl-phenyl pyridine monomers of formula (1) which can be homopolymers or copolymers. Particular monomers used in the polymerization are 4-(9-carbazoylcarbozoyl)methyl styrene, 2-(N-carbazoyl)ethyl methacrylate, and 3-(vinyl-9-ethyl)carbazole.

Conventional polymerizations of such monomers are performed. Polymerization methods are not limited and can be any one of bulk polymerization, solution polymerization, and suspension polymerization. Polymerization system can be radical polymerization, cationic polymerization or anionic polymerization. A polymerization initiator can be any conventional initiator which is generally used in the polymerization of styrene-based monomers. Particular examples of polymerization initiator include azobisisobutyronitrile (AIBN), benzoyl peroxide, hydrogen peroxide, cumyl peroxide, tert-butyl peroxide, tert-butyl hydroperoxide, lauroyl peroxide and the like. The content of 2-(4-vinyl-phenyl)pyridine can be controlled depending on the purpose in the range of from 0.01 to 99.9%.

Number average molecular weight, weight average molecular weight, and molecular weight distribution ($M_w/M_n$) of the prepared polymers are analyzed by GPC and the content of the vinyl-phenyl pyridine is analyzed by FT-NMR and FT-IR.

Examples of polymers of the present invention are the following formulas 6–8,

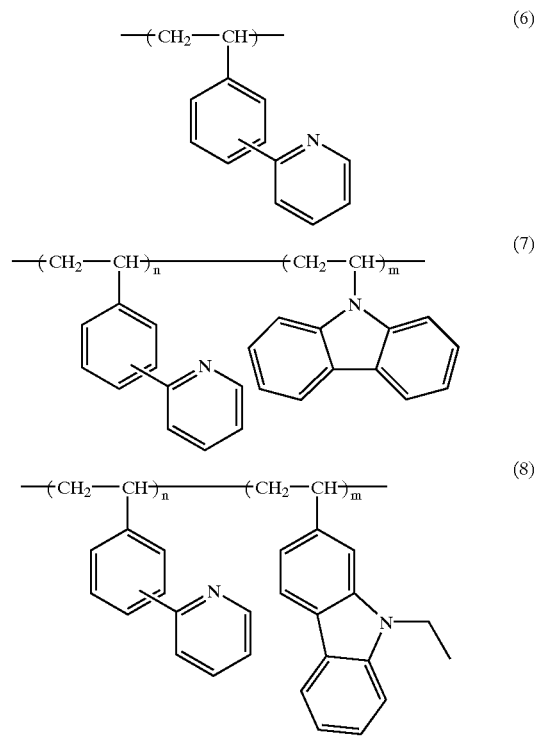

wherein n+m=100 and n is an integer of 0.01 to 99.99.

The present invention is further characterized by a complex of the prepared polymers and a metal such as iridium, ruthenium and platinum which is useful for photo-functional materials. Representative example of the complex is the following formula 9, (9)

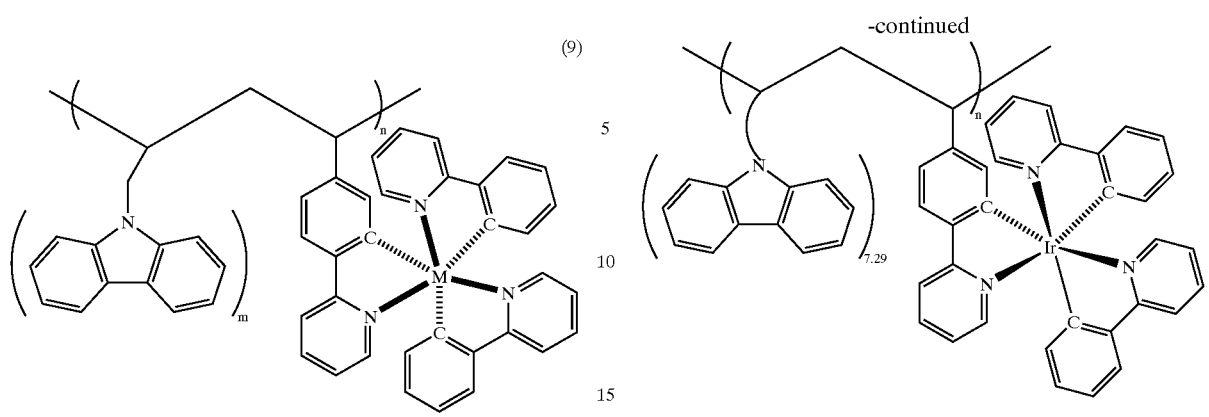

wherein M represents iridium, ruthenium or platinum; and n+m=100 and n is an integer of 0.01 to 99.99.

Example of preparation method of the polymer complex is shown in the following Scheme 3.

Scheme 3

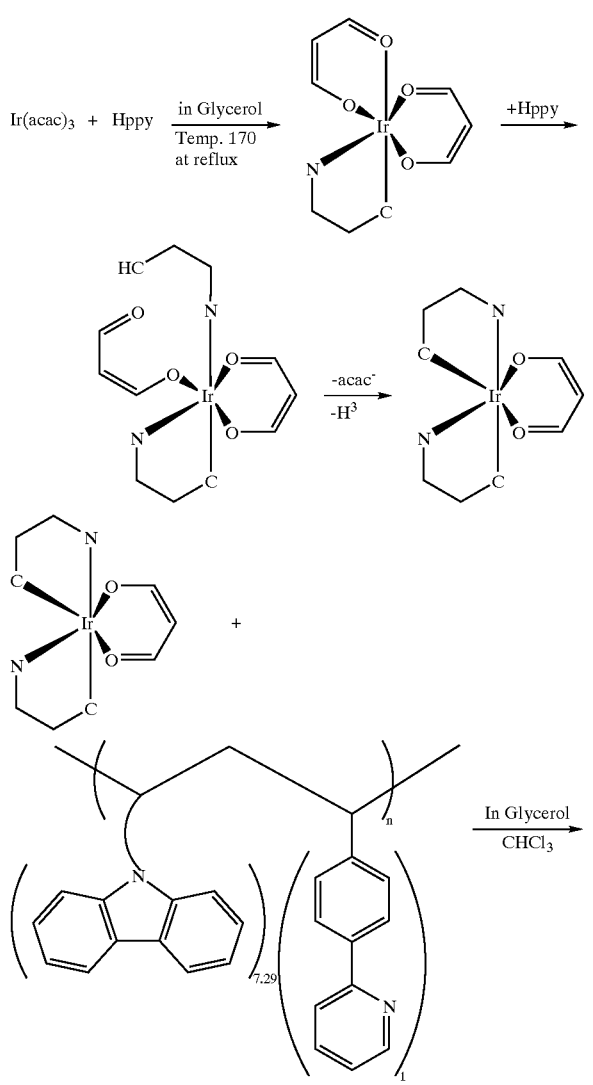

In Scheme 3, iridium (III) acetylacetonate (Iracac) and 2 equivalents of 2-phenylpyridine are reacted in glycerol and then 1 equivalent of the polymer having 2-(4-vinyl-phenyl) pyridine is added and heated at reflux. After the reaction is completed, the reaction mixture is poured into aqueous hydrogen chloride solution and then extracted with chloroform. The residue is precipitated out from chloroform/methanol solution. The crude product is purified by column chromatography and dried to obtain the desired polymer complex. Such polymer complex is very useful for photo-functional materials.

The following examples are intended to be illustrative of the present invention and should not be construed as limiting the scope of this invention defined by the appended claims.

EXAMPLE 1

Preparation of 2-(4-vinyl-phenyl)pyridine

Figure 2:
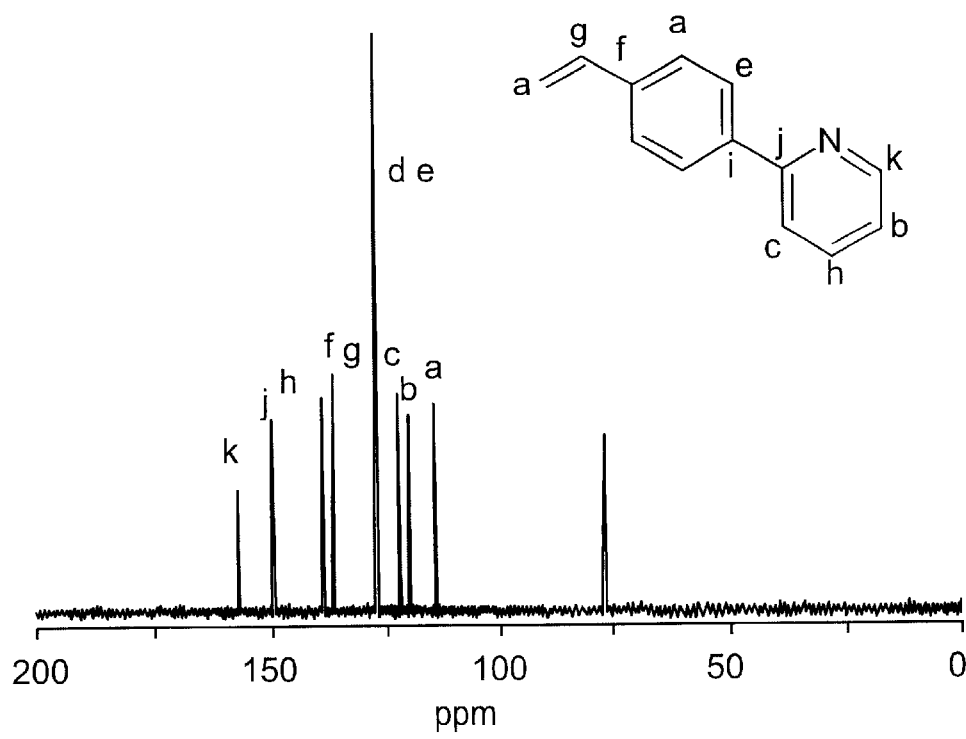
FIG. 2 represents $^{13}$C-NMR spectrum of 2-(4-vinyl-phenyl)pyridine.
Figure 3:
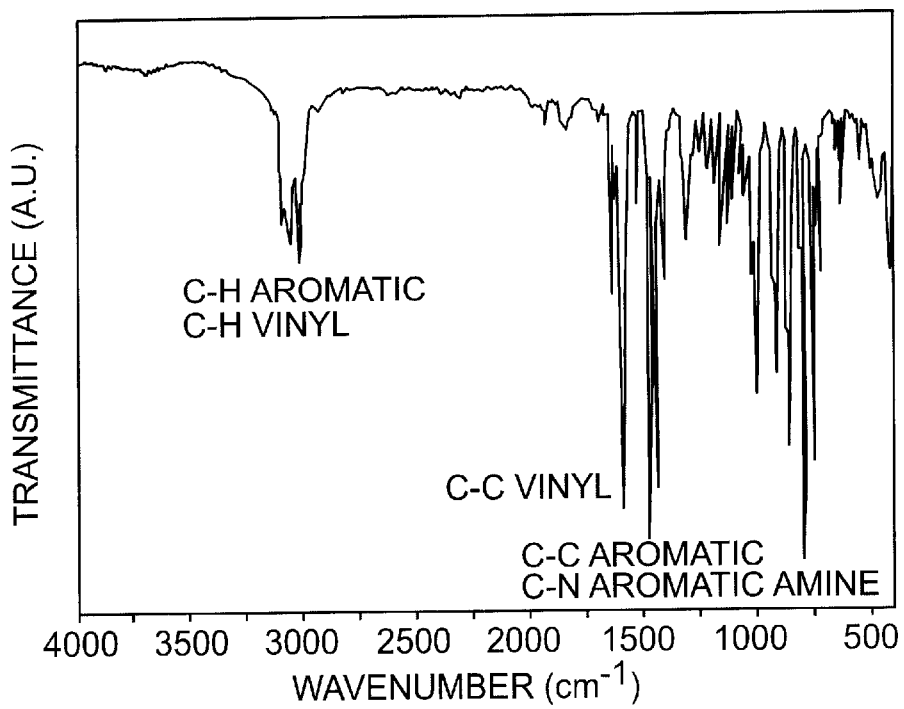
FIG. 3 represents FT-IR spectrum of 2-(4-vinyl-phenyl) pyridine.
Figure 4:
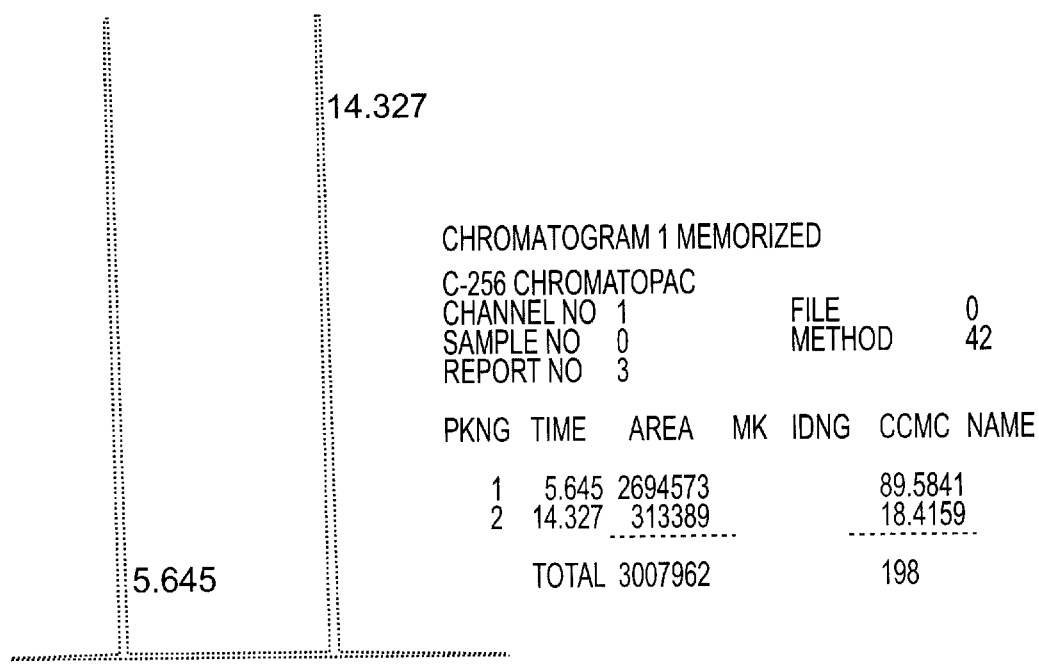
FIG. 4 represents GC spectrum of 2-(4-vinyl-phenyl) pyridine.
Figure 5:
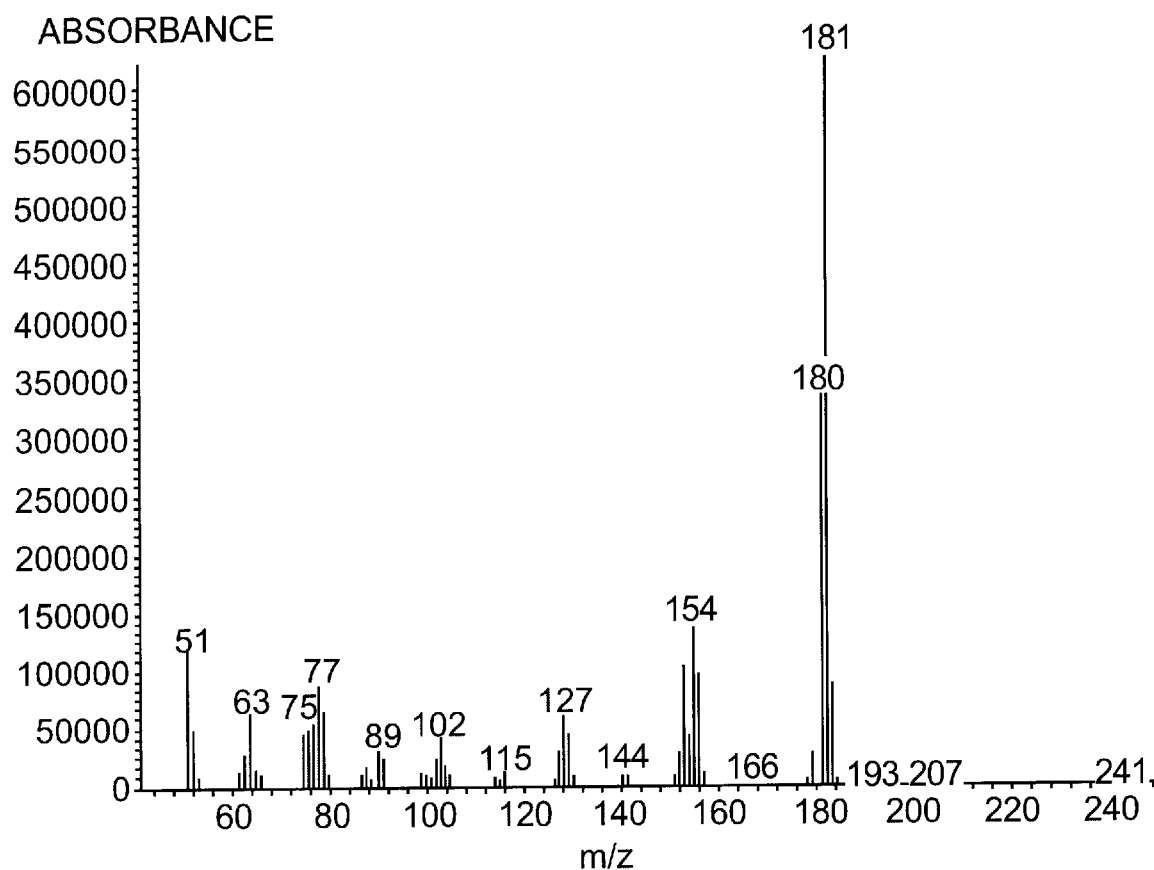
FIG. 5 represents Mass spectrum of 2-(4-vinyl-phenyl) pyridine.

4-Vinyl-phenylboronic acid (10 g, 0.0676 mol), 2-bromopyridine (12.64 g, 0.08 mol), tetrahydrofuran (100 ml), 2M potassium carbonate aqueous solution (26 ml), and tetrakis(triphenylphosphine) palladium $(Pd(Ph_3)_4$, 0.06 g, 1 mol %) were placed into 250 ml of 2-necked round-bottomed flask under $N_2$. The reaction mixture was refluxed at 80° C. for 24 hr and then poured in 200 ml of water in beaker. The reaction mixture was extracted with ether (3×150 ml) and the ether layer was then dried over magnesium sulfate (10 g) by stirring for 30 min. The dried ether layer was evaporated in vacuo to dryness and purified further by column chromatography on silica gel with eluting hexane/ethylacetate (1/9) to yield 2-(4-vinyl-phenyl) pyridine (90%).

mp: 19.3° C.; bp: 115° C./1 mmHg; $^1$H-NMR, $^{13}$C-NMR, FT-IR, GC and Mass spectra were shown in FIGS. 1–5.

EXAMPLE 2

Preparation of 2-(3-vinyl-phenyl)pyridine

The reaction was performed with 3-vinyl-phenylboronic acid (10 g, 0.0676 mol), 2-bromopyridine (12.64 g, 0.08 mol), tetrahydrofuran (100 ml), 2M potassium carbonate aqueous solution (26 ml), and tetrakis(triphenylphosphine) palladium $(Pd(Ph_3)_4$, 0.06 g, 1 mol %) according to Example 1. The yield was 80%.

EXAMPLE 3

Preparation of 2-(2-vinyl-phenyl)pyridine

The reaction was performed with 2-vinyl-phenylboronic acid (10 g, 0.0676 mol), 2-bromopyridine (12.64 g, 0.08 mol), tetrahydrofuran (100 ml), 2M potassium carbonate aqueous solution (26 ml), and tetrakis(triphenylphosphine) palladium (Pd(Ph$_3$)$_4$, 0.06 g, 1 mol %) according to Example 1. The yield was 75%.

EXAMPLE 4

Preparation of 2-(4-vinyl-phenyl)pyridine

4-Formylphenylboronic acid (10.14 g, 0.0676 mol), 2-bromopyridine (12.64 g, 0.08 mol), tetrahydrofuran (100 ml), 2M potassium carbonate aqueous solution (26 ml), and palladium acetate (Pd(OAc)$_2$, 0.04 g, 1 mol %) were placed into 250 ml of 2-necked round-bottomed flask under N$_2$. The reaction mixture was refluxed at 90° C. for 24 hr and then poured in 200 ml of water in beaker. The reaction mixture was extracted with ether (3×150 ml) and the ether layer was then dried over magnesium sulfate (10 g) by stirring for 30 min. The dried ether layer was evaporated in vacuo to dryness and purified further by column chromatography on silica gel with eluting hexane/ethylacetate (1/5) to yield 2-(4-vinyl-phenyl)pyridine (80%).

EXAMPLE 5

Preparation of 2-(4-vinyl-phenyl)pyridine

Methyltriphenylphophonium bromide (25 g, 0.07 mol), sodium hydride (NaH, 3.36 g, 0.14 mol), and toluene (100 ml) were placed into 250 ml of 2-necked round-bottomed flask under N$_2$. The reaction mixture was refluxed at 110° C. for 3 hr while changing the reaction solution to orange color. After cooling the reaction mixture, 2-(4-formyl-phenyl) pyridine (10 g, 0.0545 mol) was added and further refluxed at 110° C. for 12 hr. The reaction mixture was poured in 300 ml of water in beaker and extracted then with ether (3×150 ml). The ether layer was then dried over magnesium sulfate (10 g) by stirring for 30 min. The dried ether layer was evaporated in vacuo to dryness and purified further by column chromatography on silica gel with eluting hexane/ethylacetate (1/10) to yield 2-(4-vinyl-phenyl)pyridine (85%).

EXAMPLE 6

Figure 6:
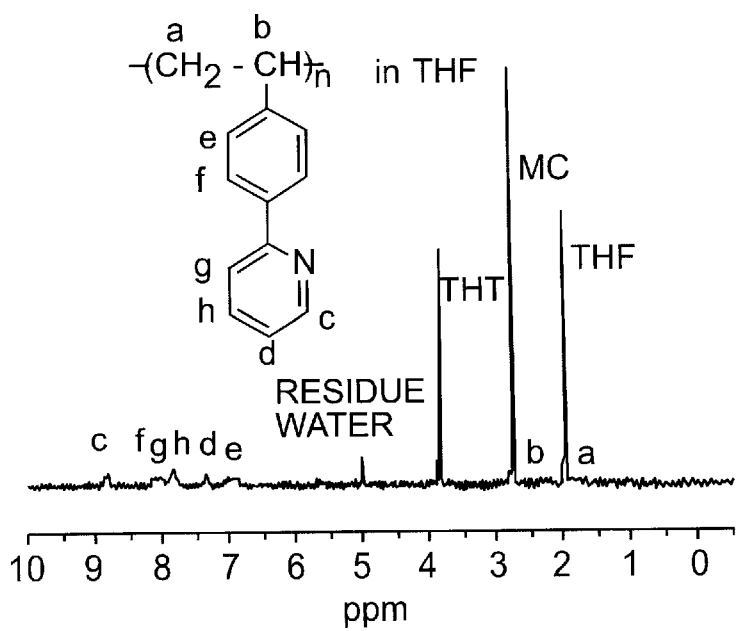
FIG. 6 represents $^1$H-NMR spectrum of poly[2-(4-vinyl-phenyl)pyridine].
Figure 7:
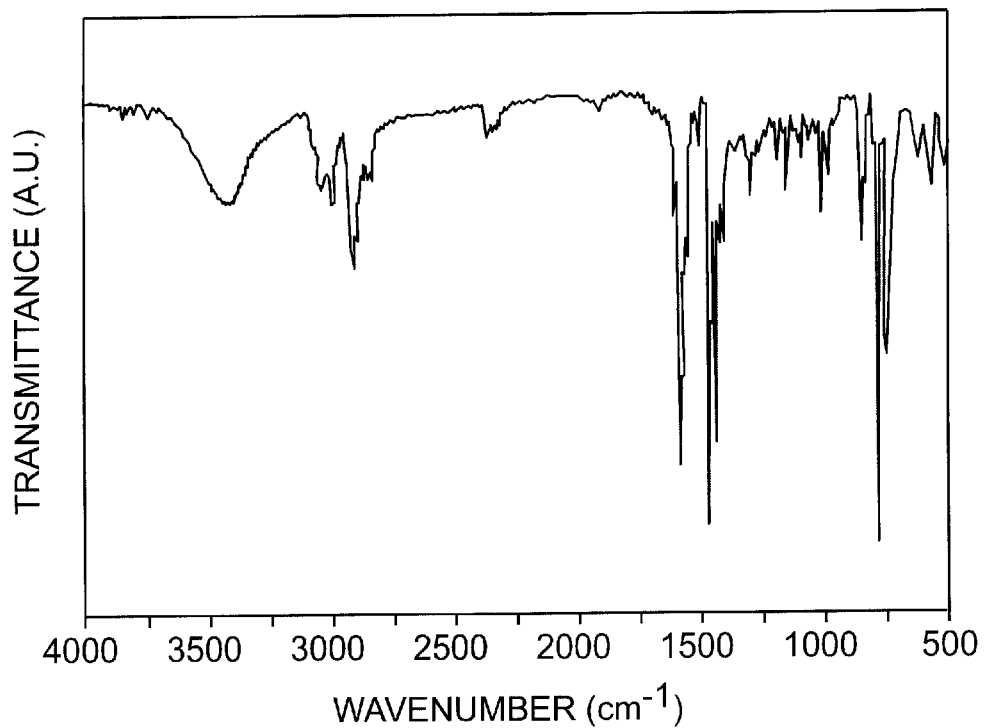
FIG. 7 represents FT-IR spectrum of poly[2-(4-vinyl-phenyl)pyridine].
Figure 8:
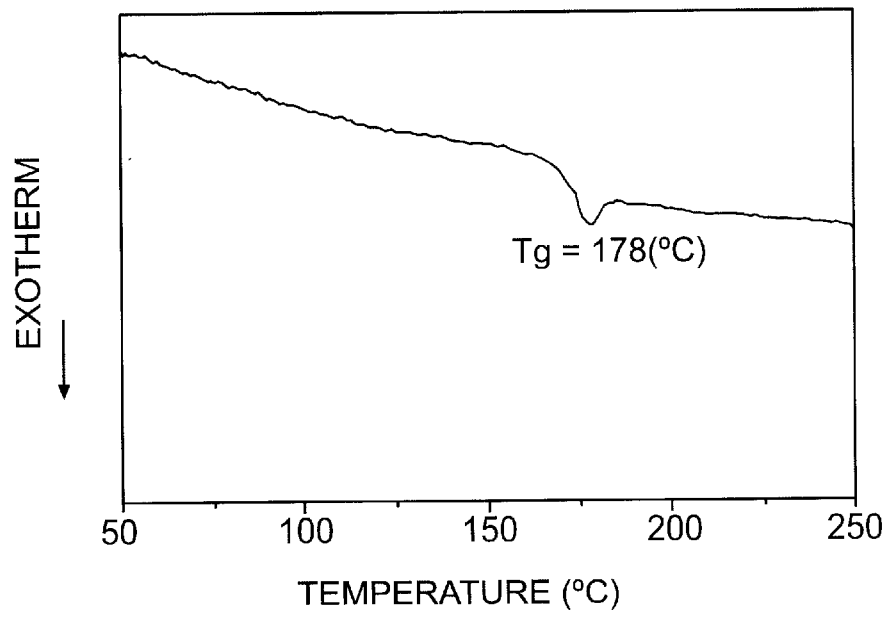
FIG. 8 represents DSC spectrum of poly[2-(4-vinyl-phenyl)pyridine].
Figure 9:
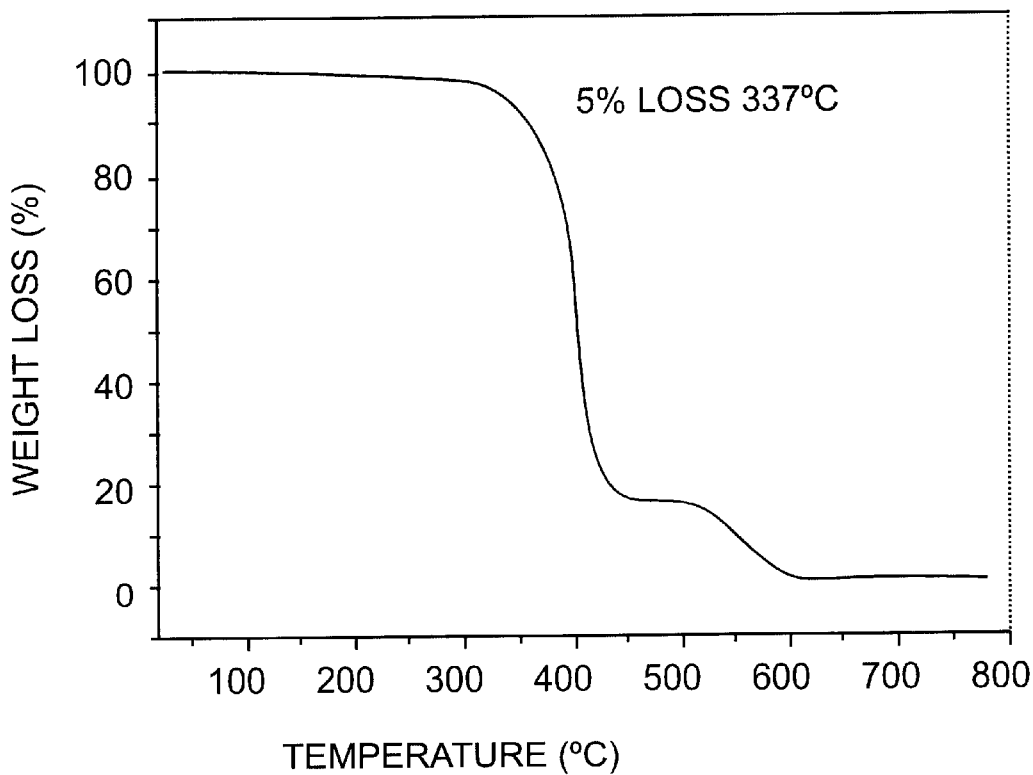
FIG. 9 represents TGA spectrum of poly[2-(4-vinyl-phenyl)pyridine].
Figure 10:
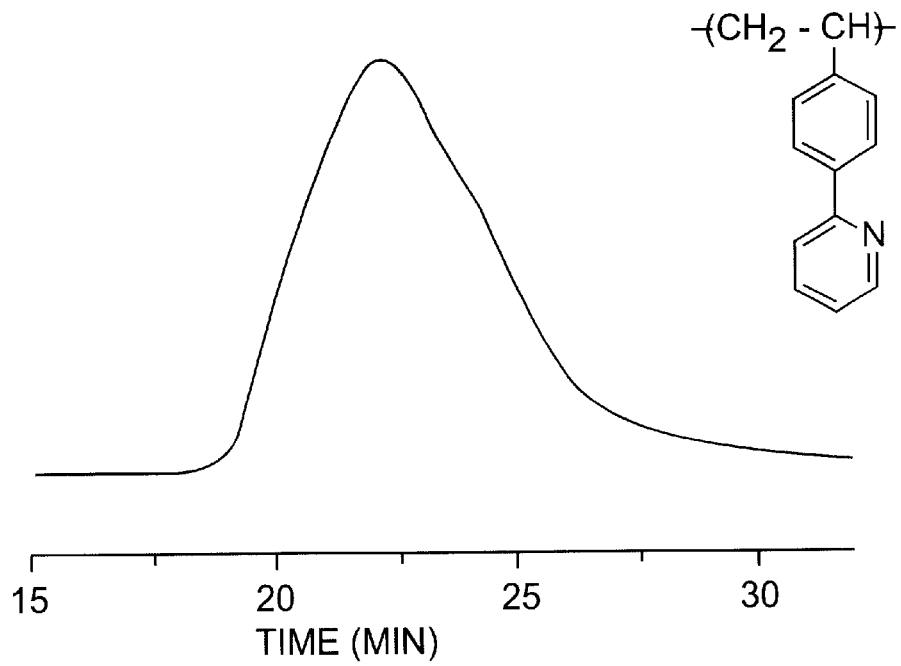
FIG. 10 represents GPC spectrum of poly[2-(4-vinyl-phenyl)pyridine].

Preparation of poly[2-(4-vinyl-phenyl)pyridine] homopolymer 2-(4-Vinyl-phenyl)pyridine (0.5 g, 2.761 mmol) and azobisisobutyronitrile (AIBN, 0.0045 g, 2.761 mmol) were placed into 10 ml of round-bottomed flask under N$_2$. The reaction mixture was bulk polymerized at 75° C. for 30 min, dissolved in chloroform (15 ml), and filtered through 0.2 μm Teflon filter. The filtrate was dropped into 200 ml of methanol to precipitate out while stirring. The precipitate was filtered through glass filter to collect the polymer product which was further dried in vacuum oven at 60° C. for 24 hr. The yield was 95%. The polymer was analyzed to have 54,000 g/mole of number average molecular weight, 230,000 g/mole of weight average molecular weight and 4.32 of molecular weight distribution (M$_w$/M$_n$). $^1$H-NMR, $^{13}$C-NMR, FT-IR, GC and Mass spectra were shown in FIGS. 6–10.

EXAMPLE 7

Figure 11:
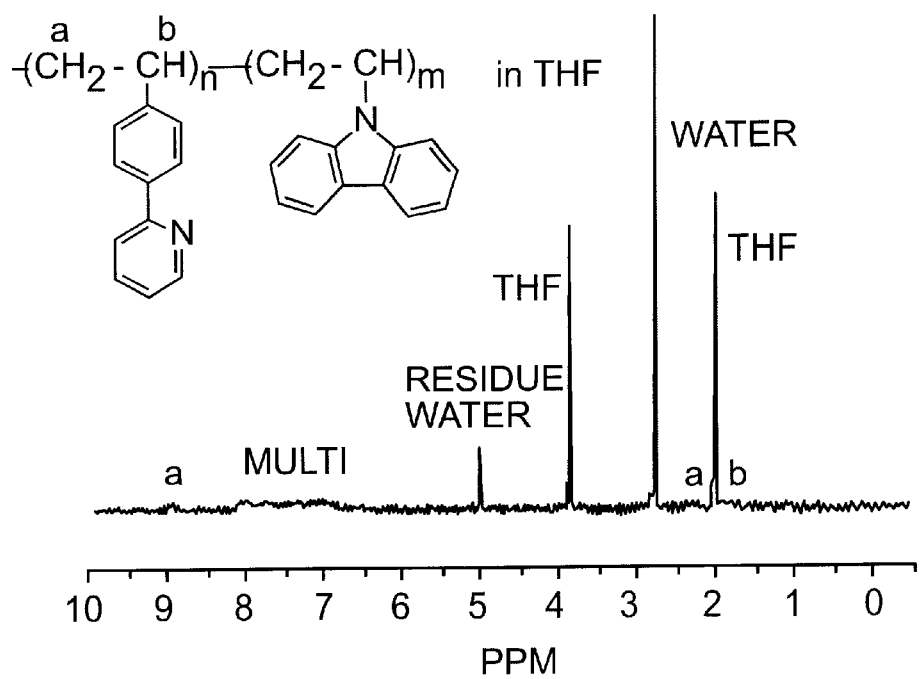
FIG. 11 represents $^1$H-NMR spectrum of poly[2-(4-vinyl-phenyl)pyridine-co-9-vinylcarbazole].
Figure 12:
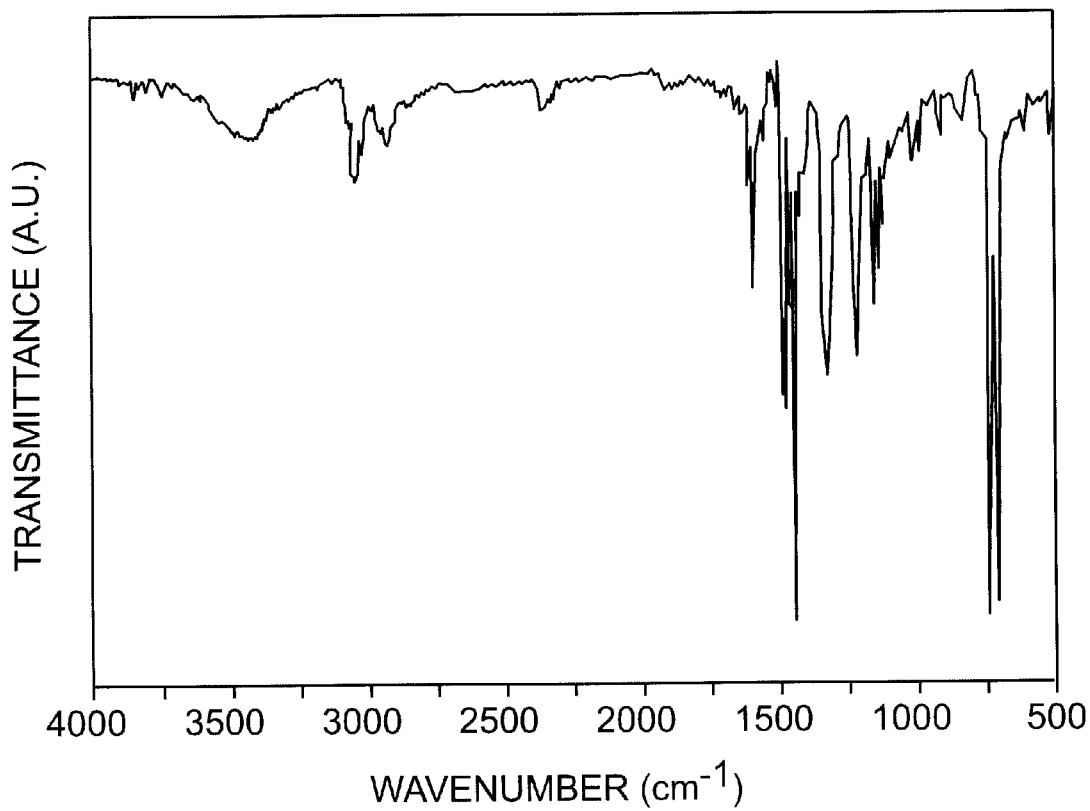
FIG. 12 represents FT-IR spectrum of poly[2-(4-vinyl-phenyl)pyridine-co-9-vinylcarbazole].
Figure 13:
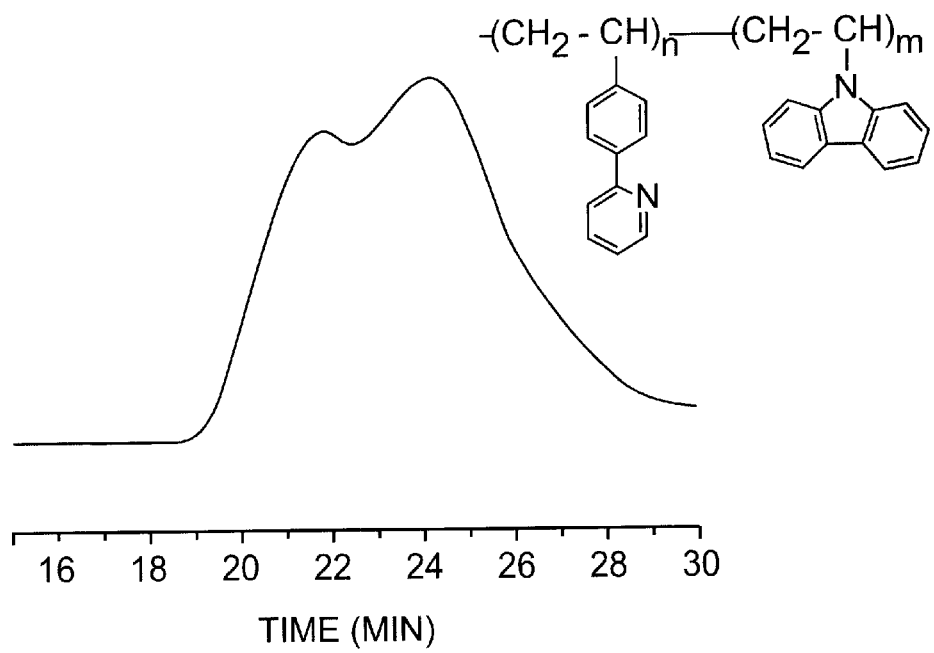
FIG. 13 represents GPC spectrum of poly[2-(4-vinyl-phenyl)pyridine-co-9-vinylcarbazole].
Figure 14:
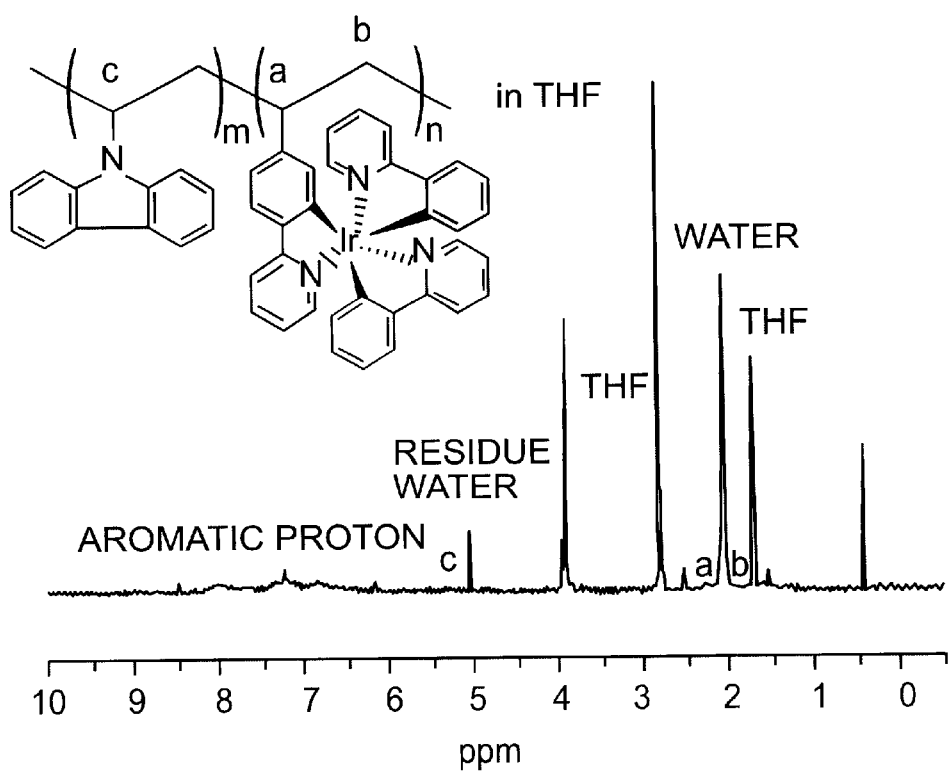
FIG. 14 represents $^1$H-NMR spectrum of poly({[2-(4-vinyl-phenyl)pyridine](phenylpyridine)$_2$iridium}-co-9-vinylcarbazole).
Figure 15:
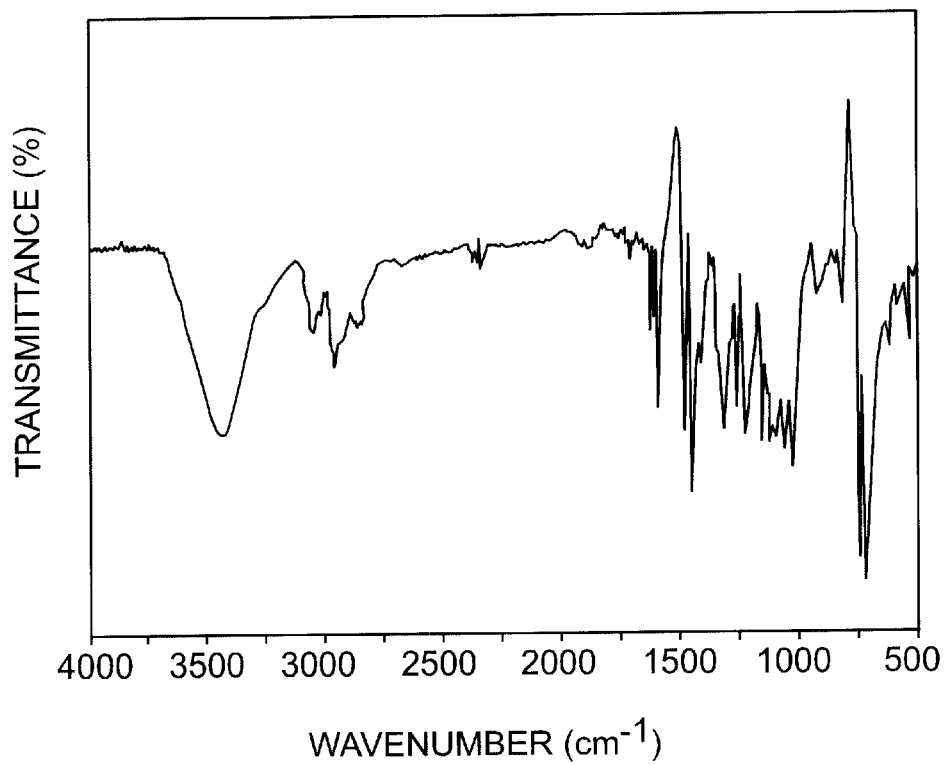
FIG. 15 represents FT-IR spectrum of poly({[2-(4-vinyl-phenyl)pyridine](phenylpyridine)$_2$iridium}-co-9-vinylcarbazole).
Figure 16:
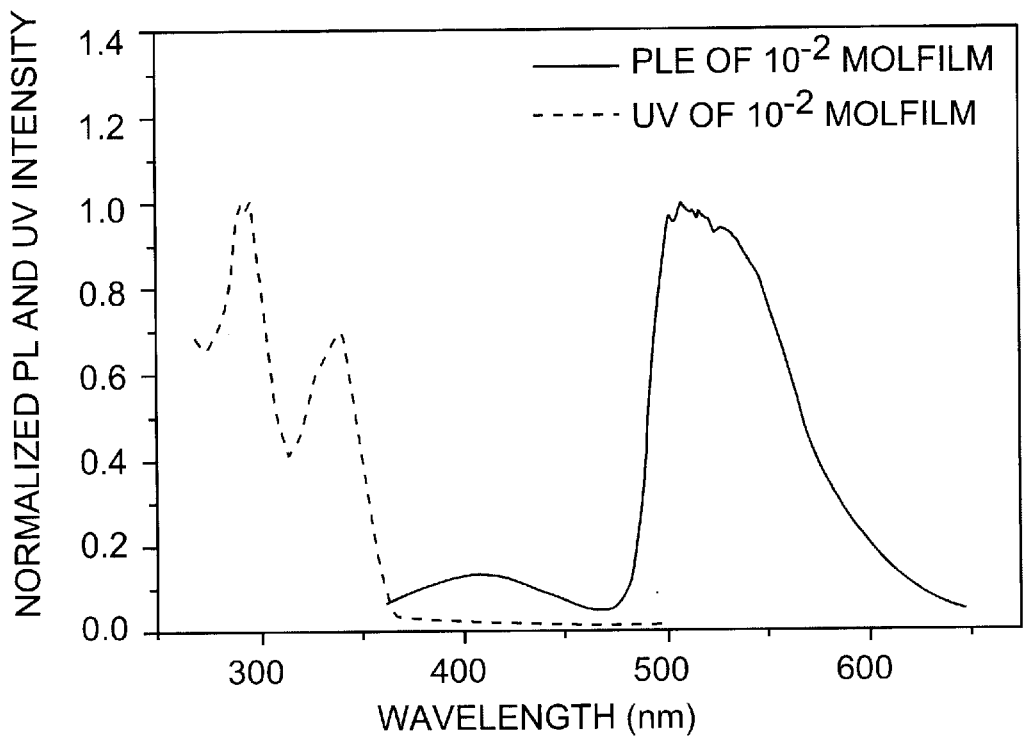
FIG. 16 represents UV and PL spectrum of poly({[2-(4-vinyl-phenyl)pyridine](phenylpyridine)$_2$iridium}-co-9-vinylcarbazole).

Preparation of poly[2-(4-vinyl-phenyl)pyridine-co-9-vinylcarbozole] copolymer 2-(4-Vinyl-phenyl)pyridine (0.5 g, 2.76 mmol), 9-vinylcarbazole (2.22 g, 10.9 mmol) and azobisisobutyronitrile (0.015 g, 1 mol %) were bulk-polymerized at 75° C. for 30 min, dissolved in chloroform (20 ml), and filtered through 0.2 μm Teflon filter. The filtrate was dropped into 250 ml of methanol to precipitate out while stirring. The precipitate was filtered through glass filter to collect the polymer product which was further dried on vacuum oven at 60° C. for 24 hr. The yield was 87%. The prepared poly[2-(4-vinyl-phenyl)pyridine-co-9-vinylcarbozole] copolymer having 20% content of 2-(4-vinyl-phenyl)pyridine was analyzed to have 43,000 g/mole of number average molecular weight, 71,000 g/mole of weight average molecular weight and 1.65 of molecular weight distribution (M$_w$/M$_n$). $^1$H-NMR, $^{13}$C-NMR, FT-IR, GC and Mass spectra were shown in FIGS. 11–16.

EXAMPLE 8

Preparation of poly[2-(4-vinyl-phenyl)pyridine-co-4-(9-carbozoyl)methyl styrene] copolymer By the same procedure as described in Example 7, poly [2-(4-vinyl-phenyl)pyridine-co-4-(9-carbozoyl)methyl styrene] copolymer having 20% content of 2-(4-vinyl-phenyl)pyridine was prepared except using 4-(9-carbazolyl) methyl styrene instead of 9-vinylcarbazole in 80%.

EXAMPLE 9

Preparation of poly[2-(4-vinyl-phenyl)pyridine-co-2-(vinyl-9-ethyl)carbozole] copolymer By the same procedure as described in Example 7, poly [2-(4-vinyl-phenyl)pyridine-co-3-(vinyl-9 -ethyl)carbozole] copolymer having 20% content of 2-(4-vinyl-phenyl) pyridine was prepared except using 2-(N-carbazoyl)ethyl methacrylate instead of 9-vinylcarbazole in 87%.

EXAMPLE 10

Preparation of poly[2-(4-vinyl-phenyl)pyridine-co-3-(vinyl-9-ethyl)carbozole] copolymer By the same procedure as described in Example 7, poly [2-(4-vinyl-phenyl)pyridine-co-2-(vinyl-9 -ethyl)carbozole] copolymer having 20% content of 2-(4-vinyl-phenyl) pyridine was prepared except using 3-(vinyl-9-ethyl) carbazole instead of 9-vinylcarbazole in 90%.

EXAMPLE 11

Preparation of poly[2-(4-vinyl-phenyl)pyridine-co-9-vinylcarbozole] copolymer

By the same procedure as described in Example 6, poly [2-(4-vinyl-phenyl)pyridine-co-9-vinylcarbozole] copolymer having 12% content of 2-(4-vinyl-phenyl)pyridine was prepared using 2-(4-vinyl-phenyl)pyridine (0.4 g, 2.2 mmol), 9-carbazole (2 g, 10.3 mmol) and azobisisobutyronitrile (0.021 g, 1 mol %). The copolymer has 22,000 g/mole of number average molecular weight, 57,000 g/mole of weight average molecular weight and 2.56 of molecular weight distribution (M$_w$/M$_n$).

EXAMPLE 12

Preparation of poly{[(2-(4-vinyl-phenyl)pyridine)(phenylpyridine)$_2$iridium]-co-9-vinyl carbazole}

Iridium(III) acetylacetonate (0.5 g, 1.02 mmol), 2-phenylpyridine (0.32 g, 2.04 mmol), and glycerol (50 ml)

were placed into 250 ml of 2-necked round-bottomed next flak. The reaction mixture was refluxed at 170° C. for 3 hr. Poly[2-(4-vinyl-phenyl)pyridine-co-9-vinylcarbozole] copolymer (0.32 g, 2.04 mmol) prepared in Example 11 and chloroform (50 ml) were added and further refluxed for 24 hr. The reaction mixture was poured into 200 ml of 1N hydrogen chloride aqueous solution and extracted with chloroform. The chloroform layer was evaporated to dryness. The residue was dissolved in chloroform (10 ml) and precipitated out from 200 ml of 99.9% methanol. The precipitate was filtered through glass filter to collect the polymer complex which was further dried on vacuum oven at 60° C. for 24 hr. The yield was 95%. The polymer was analyzed to have 43,000 g/mole of number average molecular weight, 71,000 g/mole of weight average molecular weight and 1.65 of molecular weight distribution ($M_w/M_n$). $^1$H-NMR, FT-IR, UV and PL spectra were shown in FIGS. 14–16.

Vinyl-phenyl monomers of the present invention are capable of various polymerization such as radical polymerization, cation polymerization, anion polymerization and metallocene catalyzed polymerization due to resonance effect of phenyl group unlike other monomers. Such vinyl-phenyl monomers can be polymerized to homopolymers or copolymers. Molecular weight and molecular structure of polymers can be controlled during the polymerization and the polymers with the controlled weight and structure can further incorporate with a metal such as iridium, ruthenium and platinum to form a polymer-metal complex which is useful in a variety of fields using photo-functional materials.

What is claimed is:

1. A preparing method of vinyl-phenyl monomers of formula (1) by Suzuki coupling reaction of vinyl-phenylboronic acid of formula (2) and 2-bromopyridine of formula (3) in the presence of alkali metallic base and tetrakis(triphenylphosphine) palladium

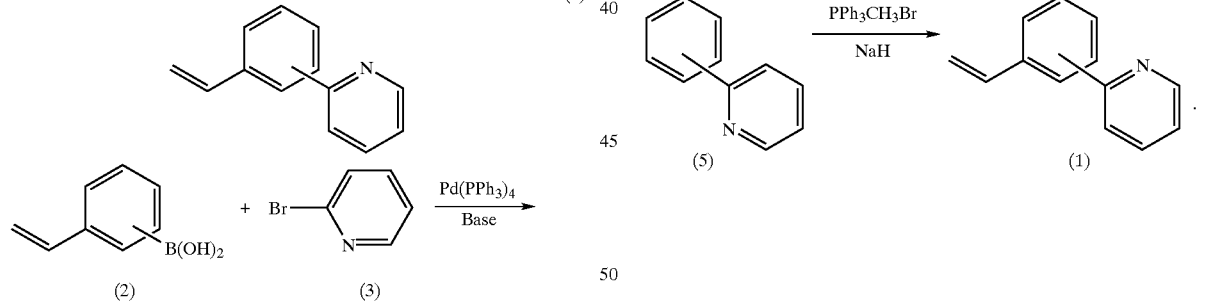

-continued

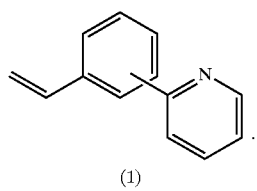

2. A preparing method of vinyl-phenyl monomers of formula (1) by Suzuki coupling reaction of formylphenylboronic acid of formula (4) and 2-bromopyridine of formula (3) in the presence of alkali metallic base and palladium catalyst to generate formylphenyl pyridine of formula (5) and further Wittig reaction of the prepared formylphenyl pyridine of formula (5) in the presence methyltriphenylphosphonium bromide (PPh$_3$CH$_3$Br) and sodium hydride.

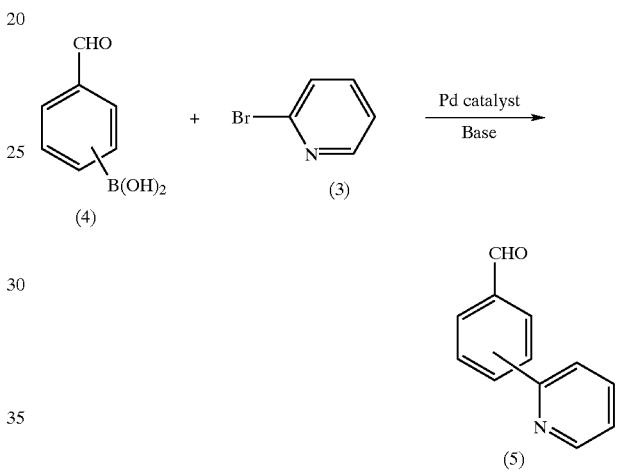

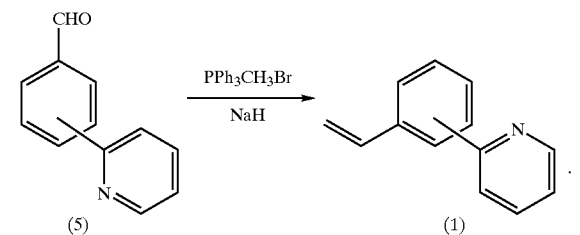

* * * * *

UNITED STATES PATENT AND TRADEMARK OFFICE
CERTIFICATE OF CORRECTION

PATENT NO. : 6,545,159 B2
DATED : April 8, 2003
INVENTOR(S) : Jae-Suk Lee et al.

It is certified that error appears in the above-identified patent and that said Letters Patent is hereby corrected as shown below:

<u>Column 12,</u>
Line 17, after "presence" insert -- of --.

Signed and Sealed this

Tenth Day of June, 2003

JAMES E. ROGAN
*Director of the United States Patent and Trademark Office*